US007015255B1

(12) United States Patent
Tomura et al.

(10) Patent No.: US 7,015,255 B1
(45) Date of Patent: Mar. 21, 2006

(54) MEDIUM OIL FOR SLURRY-BED REACTION PROCESS AND PROCESS OF PRODUCING DIMETHYL ETHER

(75) Inventors: Keiji Tomura, Tokyo (JP); Takashi Ogawa, Tokyo (JP); Masami Ono, Tokyo (JP); Keiichi Okuyama, Tokyo (JP); Seiji Aoki, Tokyo (JP); Tsutomu Shikada, Tokyo (JP); Masatsugu Mizuguchi, Tokyo (JP); Yotaro Ohno, Tokyo (JP)

(73) Assignee: JFE Holdings, Inc., Tokyo (JP)

( * ) Notice: Subject to any disclaimer, the term of this patent is extended or adjusted under 35 U.S.C. 154(b) by 0 days.

(21) Appl. No.: 10/048,640

(22) PCT Filed: Feb. 29, 2000

(86) PCT No.: PCT/JP00/01171

§ 371 (c)(1),
(2), (4) Date: Apr. 25, 2002

(87) PCT Pub. No.: WO01/10801

PCT Pub. Date: Feb. 15, 2001

(30) Foreign Application Priority Data

Aug. 3, 1999 (JP) .................................. 11/219821

(51) Int. Cl.
*C07C 27/00* (2006.01)

(52) U.S. Cl. ............................. 518/700; 585/1; 585/10; 585/12; 585/16; 585/17; 585/18
(58) Field of Classification Search ................ 518/700; 585/1, 10, 12, 16, 17, 18
See application file for complete search history.

(56) References Cited

U.S. PATENT DOCUMENTS

| 3,954,897 A | * | 5/1976 | Yamato et al. ................. 585/18 |
| 5,015,404 A | * | 5/1991 | Kubo et al. .................. 508/132 |
| 5,218,003 A | | 6/1993 | Lewnard et al. ............ 518/700 |

FOREIGN PATENT DOCUMENTS

| EP | 59/1538 A1 | 4/1994 |
| JP | 02-180983 | * 7/1990 |
| JP | 03081214 | * 4/1991 |
| JP | 9-286754 | 11/1997 |
| JP | 10273462 A | 10/1998 |
| JP | 11-130714 | 5/1999 |

OTHER PUBLICATIONS

Computer generated English translation of JP 10-273462, published Oct. 13, 1998.*
International Search Report.

* cited by examiner

Primary Examiner—Rosalynd Keys
(74) Attorney, Agent, or Firm—Sughrue Mion, PLLC

(57) ABSTRACT

(a) A medium oil wherein a main component is a hydrocarbon, and the number of paraffinic carbon atoms is 70% or more with respect to a total number of carbon atoms, (b) a medium oil wherein a main component is a polybutene, (c) a medium oil wherein a main component is a mixture of hydrocarbons of the formula (1):

$$CH_3\text{—}C(CH_3)_2\text{—}[\text{—}CH_2\text{—}C(CH_3)_2\text{—}]_n\text{—}CH_2\text{—}R \quad (1)$$

wherein R is $-CH(CH_3)_2$ or $-C(CH_3)=CH_2$, and n is 1 to 10, (d) a medium oil wherein a main component is a hydrocarbon prepared by a Fischer-Tropsch synthesis, or (e) a medium oil wherein a main component is a branched paraffinic hydrocarbon prepared by hydrogenolysis of a hydrocarbon prepared by a Fischer-Tropsch synthesis, and a process of producing dimethyl ether using the medium oil, are disclosed.

3 Claims, No Drawings

MEDIUM OIL FOR SLURRY-BED REACTION PROCESS AND PROCESS OF PRODUCING DIMETHYL ETHER

TECHNICAL FIELD

The present invention relates to a medium oil for a slurry-bed reaction process and a process of producing dimethyl ether. The term "the medium oil" as used herein means a liquid (including a substance which becomes liquid under a reaction condition) used as a medium in, for example, a slurry-bed reactor that is sometimes called an ebullating-bed reactor or a gas-liquid-solid reactor, and capable of forming a catalyst slurry of a mixture of the liquid and a solid catalyst used in the reactor.

BACKGROUND ART

In a conventional process of producing dimethyl ether, methanol is mainly used as a starting material, and the methanol is dehydrated. Recently, however, a process of synthesizing dimethyl ether directly from a raw material gas containing carbon monoxide and hydrogen was developed. According to the latter process, dimethyl ether can be produced by a progression of the chemical reaction formulae (1) and (2) as shown below in the presence of, for example, a copper-based catalyst for synthesizing methanol and a catalyst for dehydrating methanol (a catalyst for converting methanol) such as alumina. More particularly, methanol is produced from carbon monoxide and hydrogen by the catalyst for synthesizing methanol, and the resulting methanol then is dehydrated and condensed by the catalyst for dehydrating methanol to produce dimethyl ether and water. Further, as shown in the chemical reaction formula (3), the resulting water is reacted with carbon monoxide to produce carbon dioxide and hydrogen.

$$CO+2H_2 \rightarrow CH_3OH \quad (1)$$

$$2CH_3OH \rightarrow CH_3OCH_3+H_2O \quad (2)$$

$$H_2O+CO \rightarrow CO_2+H_2 \quad (3)$$

The above synthesizing reaction is an intense exothermic reaction, and there is a problem of deactivation of the catalysts used at a high temperature. Therefore, investigations of the synthesis of dimethyl ether have drawn attention to the use of a slurry-bed reaction process having advantages that a large quantity of heat can be effectively eliminated and a temperature can be easily controlled, rather than a fixed-bed reaction process having a disadvantage that an elimination of heat is relatively difficult.

In the slurry-bed reaction process, a catalyst slurry prepared by suspending catalysts in a suitable medium oil is used. The medium oil is required to have properties such as stability under the reaction condition, and an inactivity to the reaction. Further, the medium oil is desired to have other properties such that the oil is present as a liquid at a normal temperature, and thus can easily be handled, and the oil is difficult to be solidified and cause a choking in a process.

A process of producing dimethyl ether by a slurry-bed reactor is disclosed in Japanese Examined Patent Publication (Kokoku) No. 07-057739 filed by Air Products and Chemicals, Inc. (U.S.A.). The Publication discloses a paraffinic hydrocarbon or a mixture of hydrocarbons as the medium oil for forming the catalyst slurry in a reactor of the above producing process, and a purified natural mineral oil called Witco 70 is used in Example.

Further, Air Products and Chemicals, Inc. also reported, in U.S. DOE Report (DOE/PC/89865-T6), the slurry-bed synthesis of dimethyl ether, and a purified natural mineral oil called Drakeol 10 is used therein.

U.S. Pat. No. 5,459,166 by Sunggyu Lee, et al. also discloses a process of producing a gasoline component via dimethyl ether from starting materials of hydrogen and carbon monoxide by a slurry-bed reactor. In the process, a medium oil stemmed from a natural mineral oil, called Witco 40, Witco 70, or Freezene 100 is used as a slurry medium oil.

Sunggyu Lee, et al., also reported in an article [A Single-Stage, Liquid-Phase Dimethyl Ether Synthesis Process from Syngas I. Dual Catalytic Activity and Process Feasibility, Fuel Science and Technology Int'l., 9(6), 653–679 (1991)] or other articles, a dimethyl ether synthesis by a slurry-bed wherein Witco 40 or Witco 70 is used as the medium oil.

The inventors of the present invention carried out a ring analysis of the medium oils called Witco 40, Witco 70, Freezene 100, and Drakeol 10 according to an n-d-M method (ASTM D3238) and found that a % $C_P$ value (a percentage of the number of paraffinic carbon atoms with respect to a total number of carbon atoms) of each of the medium oils was less than 70.

Further, an analysis of the molecular structures of Witco 40, Witco 70, Freezene 100, and Drakeol 10 according to NMR or the like revealed that the number of branched carbon atoms, i.e., the number of carbon atoms having 3 or more carbon—carbon bonds, is 20% or more with respect to a total number of carbon atoms, in each of the above oils.

The conventional known medium oil prepared by purifying the natural mineral oil as above has a problem that an efficiency of a reaction used to produce dimethyl ether is lowered with time. For example, U.S. DOE Report (DOE/PC/89865-T6) by Air Products and Chemicals, Inc. reported that, in a slurry-bed synthesis of dimethyl ether using Drakeol 10, an amount of dimethyl ether produced was remarkably lowered with time, and the amount of dimethyl ether produced under the same conditions was lowered to about half after about 500 hours.

It was also proved that, in a slurry-bed synthesis of dimethyl ether using a conventional known medium oil such as Witco 70 or Freezene 100, the amount of dimethyl ether produced was remarkably lowered with time, as when using Drakeol 10.

Further, when the natural mineral oil as above is pyrolytically decomposed at a high temperature, a carbon residue is inevitably produced. This means that when the natural mineral oil is used as the medium oil, the catalyst may possibly be deactivated by a coking of the medium oil.

In general, from a handling standpoint, the medium oil must maintain a flowability at a suitable temperature.

The inventors of the present invention engaged in intensive research of a medium oil capable of effectively continuing a production of dimethyl ether for a long period of time in a synthesis of an oxygen-containing organic compound including dimethyl ether by a slurry-bed reactor, and found that, among the properties of the medium oil, a % $C_P$ value and an average molecular weight of the medium oil strongly influence the properties of the medium oil.

Accordingly, the object of the present invention is to remedy the defects of prior art, and to provide a medium oil which can be used in a slurry-bed reaction process, and maintain a high production of an oxygen-containing organic compound including dimethyl ether for a long period of time.

DISCLOSURE OF INVENTION

The above problem can be solved by the present invention, that is, a medium oil for a slurry-bed reaction process, characterized in that a main component is a hydrocarbon, and the number of paraffinic carbon atoms is 70% or more with respect to a total number of carbon atoms.

The present invention also relates to a medium oil for a slurry-bed reaction process, characterized in that a main component is a polybutene.

Further, the present invention relates to a medium oil for a slurry-bed reaction process, characterized in that a main component is a mixture of hydrocarbons of the formula (1):

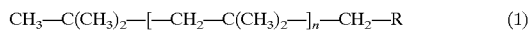

$$CH_3-C(CH_3)_2-[-CH_2-C(CH_3)_2-]_n-CH_2-R \quad (1)$$

wherein R is $-CH(CH_3)_2$ or $-C(CH_3)=CH_2$, and n is 1 to 10.

Further, the present invention also relates to a medium oil for a slurry-bed reaction process, characterized in that a main component is a hydrocarbon prepared by a Fischer-Tropsch synthesis, or a branched paraffinic hydrocarbon prepared by hydrogenolysis of a hydrocarbon prepared by a Fischer-Tropsch synthesis.

Further, the present invention also relates to a process of producing dimethyl ether, characterized by passing a mixture containing carbon monoxide and hydrogen through a catalyst slurry containing a mixture of
(1) any one of the above medium oils,
(2) a catalyst for synthesizing methanol, and
(3) a catalyst for dehydrating methanol and a catalyst for shifting, or a catalyst for dehydrating methanol and shifting.

Further, the present invention also relates to a process of producing a mixture of dimethyl ether and methanol, characterized by passing a mixture containing carbon monoxide and hydrogen through a catalyst slurry containing a mixture of
(1) any one of the above medium oils,
(2) a catalyst for synthesizing methanol, and
(3) a catalyst for dehydrating methanol and a catalyst for shifting, or a catalyst for dehydrating methanol and shifting.

BEST MODE FOR CARRYING OUT THE INVENTION

The medium oil of the present invention contains a hydrocarbon, i.e., an aliphatic hydrocarbon, an aromatic hydrocarbon, or a cycloaliphatic hydrocarbon as a main component. The term "main component" as used herein means that it accounts for 70% by weight or more, preferably 90% by weight or more of the medium oil. The medium oil of the present invention may contain, as minor components, conventional known medium oils, such as the medium oils as mentioned in the above "BACKGROUND ART" portion, in addition to the main component, the hydrocarbon. Further, the medium oil of the present invention may also contain, for example, a hydrocarbon containing oxygen, nitrogen, silicon, or halogen, or the like as an impurity, in addition to the main and minor components.

In the medium oil of the present invention, a percentage (% $C_P$) of the number of paraffinic carbon atoms contained in the present medium oil with respect to a total number of carbon atoms (i.e., a sum of the number of the carbon atoms of the hydrocarbon as the main component and the number of the carbon atoms of the minor components) contained in the present medium oil is 70% or more, preferably 80% or more. When the % $C_P$ of the medium oil is less than 70%, an efficient production of the oxygen-containing organic compound may not be maintained for a long term.

A ratio of the number of paraffinic carbon atoms with respect to a total number of carbon atoms in the medium oil can be determined by, for example, but is by no means limited to, a ring analysis according to an n-d-M method (ASTM D3238), and a ratio of the number of paraffinic carbon atoms as mentioned herein is a value determined by the n-d-M method (ASTM D3238).

The term "ring analysis" as used herein means a method used to analyze assignments (i.e., % $C_A$, % $C_N$, % $C_R$, % $C_P$) of carbon atoms in all of the compounds constituting the medium oil, according to a calculating equation prepared in advance from values of physicochemical properties of the oil, i.e., an oil composition or an oil mixture. The "% $C_A$" is a percentage of the number of aromatic carbon atoms (i.e., the number of ring carbon atoms in aromatic rings) in the oil to be assayed with respect to a total number of carbon atoms in the oil to be assayed; the "% $C_N$" is a percentage of the number of the naphthene carbon atoms (i.e., the number of ring carbon atoms in cycloaliphatic rings) in the oil to be assayed with respect to a total number of carbon atoms in the oil to be assayed; the "% $C_R$" is a percentage of the number of aromatic carbon atoms and the number of the naphthene carbon atoms in the oil to be assayed with respect to a total number of carbon atoms in the oil to be assayed; and the "% $C_P$" is a percentage of the number of paraffinic carbon atoms (i.e., the number of carbon atoms constituting saturated aliphatic hydrocarbon chains) in the oil to be assayed with respect to a total number of carbon atoms in the oil to be assayed. In the oil used in the present invention, the aliphatic hydrocarbon is composed mostly of paraffinic hydrocarbons, and rarely contains unsaturated aliphatic hydrocarbons. Therefore, the following equation:

% $C_A$+% $C_N$+% $C_P$=100 or

% $C_R$+% $C_P$=100 is satisfied.

The medium oil of the present invention wherein a main component is a hydrocarbon, and the number of paraffinic carbon atoms is 70% or more with respect to a total number of carbon atoms may be prepared, for example, by a method for separating parafins from a natural oil, by an adsorption to a molecular sieve, a method for separating parafins from a natural oil, by distillation or a combination of distillation and solvent extraction, a method for hydrogenating a natural oil, a method for production by a process having a product selectivity, i.e., a paraffin selectivity, such as a Fischer-Tropsch synthesis, or a method for polymerizing or copolymerizing an olefin such as a butene or propylene.

The medium oil of the present invention wherein the main component is a hydrocarbon, and the number of paraffinic carbon atoms is 70% or more may be a medium oil containing a polybutene as a main component. The polybutene is a liquid compound prepared by polymerizing or copolymerizing one, two or more of four isomers of butenes, that is, 1-butene, cis-2-butene, trans-2-butene, and isobutene. A preferable polybutene is prepared by polymerizing isobutene alone or copolymerizing isobutene and normal butene.

The above polymerization or copolymerization may be carried out at −20° C. to 30° C., using aluminum chloride as a catalyst.

When the medium oil of the present invention contains the polybutene as a main component, the ratio of the polybutene in the medium oil is not particularly limited, so long as the % $C_P$ of the medium oil is 70% or more, preferably 70% by weight or more, more preferably 90% by weight or more.

The polybutene is not pyrolytically decomposed even at a high temperature, but has a tendency to be depolymerized. Therefore, when the medium oil containing the polybutene as a main component is used, the oil is not pyrolytically decomposed to leave carbon residues at a high temperature, or very little deactivation of the catalyst by a coking occurs, whereas when the conventional known natural mineral oil is used, the oil is pyrolytically decomposed to produce carbon residues at a high temperature.

The medium oil of the present invention wherein the main component is the hydrocarbon, and the number of paraffinic carbon atoms is 70% or more with respect to a total number of carbon atoms, may be a medium oil wherein a main component is a mixture of the hydrocarbons of the formula (1):

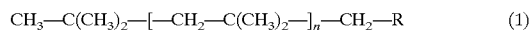

$$CH_3-C(CH_3)_2-[-CH_2-C(CH_3)_2-]_n-CH_2-R \qquad (1)$$

wherein R is —$CH(CH_3)_2$ or —$C(CH_3)=CH_2$ and, n is 1 to 10. In the mixture of the formula (1) as above, the hydrocarbon of the formula (1) wherein R is —$CH(CH_3)_2$ and the hydrocarbon of the formula (1) wherein R is —$C(CH_3)=CH_2$ may coexist, or hydrocarbons having any figures of n having 1 to 10 may coexist. The mixture may contain a small amount of hydrocarbons of the formula (1) wherein n is more than 10, so long as a weight-average molecular weight of the mixture is within the range of from 180 to 600 as mentioned below.

The medium oil of the mixture of the hydrocarbons of the formula (1) according to the present invention may be prepared, for example, by copolymerizing olefins such as isobutene.

The medium oil of the present invention wherein a main component is a hydrocarbon, and the number of paraffinic carbon atoms is 70% or more with respect to a total number of carbon atoms, may be a medium oil for a slurry-bed reaction process, characterized in that a main component is a hydrocarbon prepared by a Fischer-Tropsch synthesis, or a branched paraffinic hydrocarbon prepared by hydrogenolysis of a hydrocarbon prepared by a Fischer-Tropsch synthesis.

The Fischer-Tropsch synthesis is a process for producing a liquid hydrocarbon by a reaction of carbon monoxide and hydrogen, using a catalyst, such as an iron-based catalyst, a cobalt-based catalyst, a nickel-based catalyst, or ruthenium catalyst. The medium oil of the present invention may contain the hydrocarbon prepared by the Fischer-Tropsch synthesis as the main component, so long as the main component of the medium oil is a hydrocarbon and the number of paraffinic carbon atoms is 70% or more with respect to a total number of carbon atoms. When the number of paraffinic carbon atoms of the liquid hydrocarbon prepared by the Fischer-Tropsch synthesis is less than 70% with respect to a total number of carbon atoms, the number of paraffinic carbon atoms can be increased to 70% or more with respect to a total number of carbon atoms by hydrogenolysis. Thus, the resulting branched paraffinic hydrocarbon as above may be used as the medium oil of the present invention.

The Fischer-Tropsch synthesis has an advantage that a liquid aliphatic hydrocarbon having about 5 to 30 carbon atoms can be produced.

A weight-average molecular weight of the medium oil of the present invention is not particularly limited, but is preferably 180 to 600, more preferably 180 to 400, most preferably 180 to 350. When the weight-average molecular weight of the medium oil is less than 180, an excessive amount of the medium oil is vaporized, and thus the capacities of a trap placed downstream of the reactor for the vaporized medium oil and a pump placed downstream of the reactor for the medium oil must be increased, and therefore, the plant cost is raised. Further, it may become difficult to control an amount of the medium oil and the temperature. When the weight-average molecular weight of the medium oil is more than 600, the viscosity of the medium oil may be increased, and a process may be choked by oil scattered downstream of the reactor.

The weight-average molecular weight of the medium oil of the present invention may be determined, for example, by a mass spectrometer or a gel permeation chromatography.

A pour point of the medium oil of the present invention is not particularly limited, but preferably is −10° C. or less, more preferably −20° C., particularly preferably −30° C. When the pour point is lower than −10° C., the medium oil may be solidified at a normal temperature or a general winter temperature. Thus, it may become necessary to maintain a temperature of a piping system and the plant cost may be raised, or a workability, such as a handling, of the medium oil may become difficult.

The pour point can be determined, for example, by JIS K 2269. The pour point disclosed herein is determined according to JIS K 2269.

A viscosity of the medium oil of the present invention is not particularly limited, but preferably is 0.05 to 2 cP at a reaction temperature. When the viscosity of the medium oil is much more than 2 cP, a traveling rate of raw material gases or products dissolved in a liquid phase of the slurry-bed reaction layer may be lowered, and thus, the reaction rate may be lowered. When the viscosity of the medium oil is much less than 0.05 cP, the catalysts may reach a state of being easily settled, and a dispersion of the catalysts may be affected. Therefore, a degree of contact between the catalysts and the raw material gases may be lowered and a reaction rate may be decreased. The viscosity can be determined by, for example, a measurement of a kinematic coefficient of viscosity and a specific gravity, and then a calculation therefrom. The viscosity disclosed herein is determined by the above method.

A sulfur content of the medium oil of the present invention is preferably several parts per million or less, more preferably 1 ppm or less. When the sulfur content of the medium oil is more than the above scope, the catalysts may be affected by sulfur and the activity thereof may be lowered.

A 50% running point (i.e., a temperature at which 50% of an oil is vaporized under a normal pressure) of the medium oil of the present invention is preferably 230° C. or more. When the 50% running point is low, and thus a large amount of the medium oil is vaporized at a reaction temperature and a reaction pressure, an increase of a capacity of a trap placed downstream of a reactor for the vaporized medium oil may be required, and the plant cost may be raised. Also, it may become difficult to control an monoxide and hydrogen.

The medium oil of the present invention may be preferably used in a slurry-bed reaction process of producing an oxygen-containing organic compound from a raw material gas containing carbon monoxide and hydrogen. The oxygen-containing organic compound may be, for example, an ether, such as dimethyl ether, methyl tertiary-butyl ether, ethyl tertiary-butyl ether, or tertiary-amyl ether, an alcohol, such as methanol or ethanol, dimethyl carbonate, acetaldehyde, a carboxylic acid such as acetic acid, dimethoxymethane or dimethoxyethane. Besides the oxygen-containing organic compound, the medium oil of the present invention may be used to produce an olefin such as propylene or ethylene, or a hydrocarbon such as a gasoline component. The production includes not only a synthesis of the hydrocarbon or the oxygen-containing organic compound as a final product, but also a synthesis of the hydrocarbon or the oxygen-containing organic compound as a reaction intermediate.

A conventional known process of producing dimethyl ether can be applied to the process of producing dimethyl ether according to the present invention, as it is, except that the medium oil of the present invention is used as a medium oil. More particularly, dimethyl ether can be produced by passing the raw material gas containing carbon monoxide and hydrogen through a catalyst slurry layer composed of a mixture of the medium oil of the present invention, a catalyst for synthesizing methanol, and a catalyst for dehydrating methanol or a catalyst for dehydrating methanol and shifting. Further, the present invention can be also applied to a process wherein a catalyst has three functions of synthesizing methanol, dehydrating methanol, and shifting.

The raw material gas may be supplied by a gasification of coal, or a reforming of methane, and a reaction temperature is preferably 150° C. to 400° C., more preferably 250° C. to 300° C. A reaction pressure is preferably 1 to 15 Mpa, more preferably 3 to 7 Mpa. An amount of the catalyst in the medium oil is preferably 1 to 50% by weight, more preferably 10 to 30% by weight, with respect to the medium oil.

In the process of producing dimethyl ether according to the present invention, a known catalyst for synthesizing methanol, such as a catalyst of the composition formula:

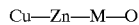

Cu—Zn—M—O wherein M is one or more metal atoms selected from the group consisting of aluminum, silicon, titanium, zirconium, chromium, cerium, and gallium, may be used as the catalyst for synthesizing methanol.

In the process of producing dimethyl ether according to the present invention, a known catalyst for dehydrating methanol, such as a methanol-dehydrating catalyst containing alumina as a main component, or a methanol-dehydrating catalyst containing silica, silica-alumina or zeolite as a main component, may be used. In the process of producing dimethyl ether according to the present invention, copper, zinc, iron, chromium, or the like may be used as the shifting catalyst.

In the process of producing dimethyl ether according to the present invention, a methanol-dehydrating and shifting catalyst may be used instead of the combination of the methanol-dehydrating catalyst and the shifting catalyst. The methanol-dehydrating and shifting catalyst has a function of dehydrating methanol and a function of shifting. amount of the medium oil in a reactor, and a reaction.

Of other properties of the medium oil, a solubility or a solubilizing rate of a raw material, a product, or a reaction intermediate may influence the reaction. More particularly, when dimethyl ether is produced, a solubility and a solubilizing rate, to the medium oil, of the raw material gas such as carbon monoxide or hydrogen, the reaction intermediate such as methanol or water, and the product such as dimethyl ether and carbon dioxide are the properties which may influence the reaction.

When the solubility or the solubilizing rate of the raw material gas to the medium oil is low, an efficiency of a conversion of the raw material gas after reaching the catalysts is lowered. When the solubility of the product such as dimethyl ether or carbon dioxide is high, reactions on the catalyst to produce dimethyl ether, carbon dioxide or the like do not easily proceed. Further, it is preferable that, shortly after the reaction intermediate such as water or methanol is formed, the intermediate arrives at an active site of the catalyst subsequently used, and then is converted. The medium oil of the present invention can satisfy such requirements for the solubility and the solubilizing rate as above.

The medium oil of the present invention is used in a slurry-bed reaction process. In the present invention, the slurry-bed reaction process is not particularly limited, so long as it is carried out in a catalyst slurry composed of a mixture of a solid catalyst and the medium oil. The slurry-bed reaction process may be, for example, a process of synthesizing an organic compound (hydrocarbon) or an oxygen-containing organic compound from another organic compound (hydrocarbon) or a raw material gas containing carbon For example, a catalyst prepared by imparting a shifting function of copper to the methanol-dehydrating catalyst as above, i.e., a methanol-dehydrating and shifting catalyst (the composition formula: Cu—Al—O) containing a copper oxide and an alumina as a main component, a methanol-dehydrating and shifting catalyst (the composition formula: Cu—Si—O) containing a copper oxide and a silicon oxide, or a methanol-dehydrating and shifting catalyst (the composition formula: Cu—Si—Al—O) containing a copper oxide and a silica-alumina may be used.

The product of the process of the present invention can be isolated and purified by a usual method.

A conventional known process of producing a mixture of dimethyl ether and methanol can be applied to the process of producing a mixture of dimethyl ether and methanol according to the present invention, as it is, except that the medium oil of the present invention is used as a medium oil. More particularly, the mixture of dimethyl ether and methanol can be produced by passing the raw material gas containing carbon monoxide and hydrogen through a catalyst slurry layer composed of a mixture of the medium oil of the present invention, a catalyst for synthesizing methanol, and a catalyst for dehydrating methanol or a catalyst for dehydrating methanol and shifting. Further, the present invention can be also applied to a process wherein a catalyst having three functions of synthesizing methanol, dehydrating methanol, and shifting.

The raw material gas, the methanol-synthesizing catalyst, the methanol-dehydrating catalyst, and the methanol-dehydrating and shifting catalyst which are used in the process of producing the mixture may be the same as those used in the process of producing dimethyl ether. However, when the mixture of dimethyl ether and methanol is produced, it is preferable to use a silica based or silica-alumina based catalyst for dehydrating methanol and a silica based or silica-alumina based catalyst for shifting, or a methanol-dehydrating and shifting catalyst containing a silica as a main component, or a methanol-dehydrating and shifting catalyst containing a silica-alumina as a main component.

EXAMPLES

The present invention now will be further illustrated by, but is by no means limited to, the following Examples.

Examples 1 to 7

Seven polybutenes having different physical properties such as a weight-average molecular weight were prepared. A mixture of n-butene and isobutene (containing a small amount of butane) was used as a starting material, and polymerized by an aluminum chloride catalyst and water (as an auxiliary catalyst) at −20° C. to 30° C. The product was saturated by adding hydrogen, and purified. The physical properties such as a weight-average molecular weight were changed by varying a composition of the raw material, the polymerizing temperature and/or the purification (fractional distillation) condition.

The chemical properties of the resulting medium oil were determined by the following methods. The weight-average molecular weight of the medium oil was determined by a mass spectrometer and a gel permeation chromatography. The percentage (% $C_P$) of the number of paraffinic carbon atoms with respect to a total number of carbon atoms of the medium oil was determined by an n-d-M method (ASTM D3238). The viscosity at 260° C. was determined by a kinematic coefficient of viscosity and a specific gravity. The pour point was determined by JIS K 2269. The results are shown in Table 1. Further, the sulfur content of each of the resulting medium oils was not more than 1 ppm.

Comparative Example

Determination of Chemical Properties of Comparative Medium Oils

Various chemical properties of commercially available oils, i.e., Witco 70 (Witco), Witco Freezene Heavy (Witco F.H.; Witco), and Drakeol 10 (Penreco) were determined according to the methods disclosed in Example 1. The results are shown in Table 1. Further, the sulfur content of each of three medium oils was not more than 1 ppm, respectively.

The medium oil, Witco F.H., used in this Comparative Example belongs to a same series as that of Freezene 100 disclosed in the "BACKGROUND ART", but has a fraction (an average molecular weight) different therefrom.

TABLE 1

|  | Average molecular weight (g/mol) | % $C_P$ (%) | Viscosity (cP; at 260° C.) | Pour point (° C.) | 50% running point (° C.) |
|---|---|---|---|---|---|
| Example 1 | 180 | 83 | 0.3 | <−70 | 190 |
| Example 2 | 220 | 83 | 0.4 | <−70 | 240 |
| Example 3 | 300 | 80 | 0.7 | <−40 | 300 |
| Example 4 | 370 | 84 | 1.2 | −35 | <500 |
| Example 5 | 400 | 84 | 1.5 | −30 | <500 |
| Example 6 | 430 | 77 | 1.6 | −30 | <500 |
| Example 7 | 580 | 77 | 2.4 | −25 | <500 |
| Witco 70 | 310 | 65 | 0.8 | <−5 | 363 |
| Witco F.H. | 390 | 58 | 1.8 | −30 | 440 |
| Drakeol 10 | 360 | 65 | 0.5 | −9 | 410 |

In the columns of the pour point and the 50% running point, "<" means that a concrete value was not determined, but indicates only the fact that a value less than the listed value was confirmed.

Preparation Example 1

Preparation of Dimethyl Ether and Evaluation of Production Efficiency

To a laboratory device equipped with a 100 mL reactor, 24 g of the medium oil prepared in Example 1 was charged, and then, 2.4 g of a copper-zinc-alumina-based catalyst for synthesizing methanol (CuO/ZnO/$Al_2O_3$:31/16/53) and 1.2 g of a methanol-dehydrating and shifting catalyst (CuO/$Al_2O_3$) containing an alumina as a main component were added. A weight ratio of the catalyst for synthesizing methanol and the methanol-dehydrating and shifting catalyst [the catalyst for synthesizing methanol:the methanol-dehydrating and shifting catalyst] was 2:1. After the whole was changed to a slurry state, the reactor was sealed. A reaction to produce dimethyl ether was carried out by passing a raw material gas [carbon monoxide:hydrogen gas:carbon dioxide=47.5:47.5:5 (volume ratio)] at a passing rate of 340 NmL/minute through the slurry in the reactor while the slurry was agitated, at which time a reaction temperature was 260° C., and a reaction pressure was 5 MPa.

Before carrying out the reaction to produce dimethyl ether, a preliminary reducing procedure was carried out to thereby convert the catalysts into suitable reduced states, by passing a gas mixture, $H_2/N_2$, at about 200° C. for 4 hours under a normal pressure.

While carrying out the reaction to produce dimethyl ether, flow rates of the gases (the resulting gases) passing through the reactor were measured by a gas meter, and compositions of the resulting gases were analyzed by a chromatography. From the results, a percentage (unit=%) of conversion of carbon monoxide, and a yield of dimethyl ether (unit=mol/g catalyst·hour) were calculated by following equations:

Conversion rate of carbon monoxide=$100 \times (V_{in} - V_{out})/V_{in}$ wherein $V_{in}$ denotes a flow rate of carbon monoxide in the raw material gas, $V_{out}$ denotes a flow rate of carbon monoxide in the resulting gas.

Yield of dimethyl ether=$W_{DME}/W_{cat}$ wherein $W_{DME}$ denotes a yield of dimethyl ether per hour, and $W_{cat}$ denotes a weight of the catalyst.

Table 2 shows, (1) the conversion rate of carbon monoxide (CO) (unit=%), after 30 hours from the beginning of the reaction, (2) the yield of dimethyl ether (DME) (unit=mol/g catalyst·hour) after 30 hours from the beginning of the reaction, and (3) a lowered rate (unit=%) of a yield of dimethyl ether. The lowered rate of a yield of dimethyl ether as shown in the item (3) is a reduced ratio [=(A−B)/A] of a yield (B) of dimethyl ether after 130 hours from the beginning of the reaction, to a yield (A) of dimethyl ether after 30 hours from the beginning of the reaction.

The procedures disclosed in Preparation Example 1 were repeated, except that the medium oils prepared in Examples 2 to 7, or the medium oil used in the Comparative Example were used instead of the medium oil prepared in Example 1. The results are shown in Table 2. Further, for the medium oil prepared in Example 3 and Witco 70, a lowered rate [=(A−C)/A] of a yield (C) of dimethyl ether after 300 hours from the beginning of the reaction, to a yield (A) of dimethyl ether after 30 hours from the beginning of the reaction was obtained. The results are shown in Table 3.

TABLE 2

| | CO conversion rate after 30 hours | DME yield after 30 hours | Lowered rate of DME yields between 30 hours later and 130 hours later |
|---|---|---|---|
| Example 1 | 55 | 21 | 1.5 |
| Example 2 | 55 | 22 | 1.4 |
| Example 3 | 56 | 22 | 1.7 |
| Example 4 | 47 | 18 | 3.5 |
| Example 5 | 47 | 18 | 4.2 |
| Example 6 | 47 | 18 | 8 |
| Example 7 | 45 | 17 | 9 |
| Witco 70 | 47 | 18 | 28 |
| Witco F.H. | 44 | 17 | 33 |
| Drakeol 10 | 44 | 17 | 17 |

TABLE 3

| | Lowered rate of DME yield between 30 hours later and 300 hours later |
|---|---|
| Example 3 | 3.4 |
| Witco 70 | 43 |

As apparent from Table 2, the experiment results obtained after 30 hours from the beginning of the reaction show that the medium oils prepared in Example 1 to 3 were particularly excellent as to the conversion rate of carbon monoxide and a yield of dimethyl ether.

Further, Table 2 shows the lowered rate between the yield of dimethyl ether after 30 hours from the beginning of the reaction and the yield of dimethyl ether after 130 hours from the beginning of the reaction. The results indicate that the lowered rates of the Comparative oils were remarkably poor and inferior, whereas the lowered rates of the medium oils prepared in Examples 1 to 7 were very small. Of the medium oils of the present invention, the medium oils prepared in Example 1 to 3 had a particularly excellent property (lowered rate=1.4 to 1.7%), and the medium oil prepared in Example 4 or 5 had secondary excellent property (lowered rate=3.5 and 4.2%).

As mentioned above, the results obtained from the medium oils prepared in Examples 1 to 7 show that, when the medium oil of the present invention is used, a production efficiency of dimethyl ether can be enhanced at an initial stage of the reaction, and maintained at a high level for a long term.

On the contrary, the results obtained from the medium oils used in the Comparative Example show that, when the medium oil not satisfying the requirements of the present invention is used, a production efficiency of dimethyl ether is relatively low at an initial stage of the reaction and becomes remarkably lowered. Therefore, a catalyst slurry must be changed every several hours to restore the production efficiency of dimethyl ether, and this results in a significant increase of a production cost.

Example 8

The medium oil of the present invention was prepared by the Fischer-Tropsch synthesis. More particularly, a liquid hydrocarbon was prepared by reacting carbon monoxide and hydrogen (molar ratio=about 1:2) under about 20 atmospheric pressure at about 320° C., using a melted iron catalyst, and a hydrogenolysis thereof was carried out to obtain a branched paraffinic hydrocarbon. The chemical properties of the resulting medium oil were determined according to the same methods as those disclosed in Examples 1 to 7. The results are shown in Table 4.

As a comparative medium oil, a commercially available oil, Witco 40 (Witco) was used. The chemical properties determined by the same methods as those disclosed in Examples 1 to 7. The results are shown in Table 4. Further, the sulfur content of Witco 40 was not more than 1 ppm.

TABLE 4

| | Average molecular weight (g/mol) | % $C_P$ (%) | Viscosity (cP; at 260° C.) | Pour point (° C.) | 50% running point (° C.) |
|---|---|---|---|---|---|
| Example 8 | 440 | 93 | 0.4 | <−10 | 420 |
| Witco 40 | 240 | 64 | 0.5 | −1 | 320 |

In the column showing the pour point, "<" means that a concrete value was not determined, but indicates only that a value less than the listed value was confirmed.

Subsequently, dimethyl ether was prepared and a production efficiency was evaluated according to the same methods as those disclosed in Preparation Example 1. The results are shown in Table 5.

TABLE 5

| | CO conversion rate after 30 hours | DME yield after 30 hours | Lowered rate of DME yields between 30 hours later and 130 hours later |
|---|---|---|---|
| Example 8 | 38 | 15 | 9 |
| Witco 40 | 49 | 19 | 15 |

As apparent from Table 5, the Fischer-Tropsch synthesis oil prepared in Example 8 exhibited a low yield of dimethyl ether at an early stage, but an excellent result of a low reducing rate of a yield of dimethyl ether. Witco 40 oil exhibited a high yield of dimethyl ether at an early stage, but a lowered rate of a yield of dimethyl ether was bad, and not preferable from a standpoint of a catalytic stability.

Preparation Example 2

Preparation of Dimethyl Ether/Methanol and Evaluation of Production Efficiency

To a laboratory device equipped with a 100 mL reactor, 24 g of the medium oil prepared in Example 3 was charged, and then 2.4 g of a copper-zinc-alumina-based catalyst for synthesizing methanol (CuO/ZnO/$Al_2O_3$:31/16/53) and 1.2 g of a methanol-dehydrating and shifting catalyst (CuO/$SiO_2$.$Al_2O_3$) containing a silica as a main component were added. A weight ratio of the catalyst for synthesizing methanol and the methanol-dehydrating and shifting catalyst [the catalyst for synthesizing methanol:the methanol-dehydrating and shifting catalyst] was 2:1. After the whole was changed to a slurry state, the reactor was sealed. A reaction to produce a mixture of dimethyl ether and methanol was carried out by passing a raw material gas [carbon monoxide:hydrogen gas:carbon dioxide=47.5:47.5:5 (volume ratio)] at a passing rate of 340 NmL/minute through the slurry in the reactor while the slurry was agitated, at which time a reaction temperature was 260° C., and a reaction pressure was 5 MPa.

Before carrying out the reaction to produce a mixture of dimethyl ether and methanol, a preliminary reducing procedure was carried out to thereby convert the catalysts into suitable reduced states, by passing a gas mixture, $H_2/N_2$, at about 200° C. for 4 hours under a normal pressure.

While carrying out the reaction to produce a mixture of dimethyl ether and methanol, the flow rates of the gases (the resulting gases) passing through the reactor were measured by a gas meter, and the compositions of the resulting gases were analyzed by a chromatography. From the results, a percentage (unit=%) of conversion of carbon monoxide, and a yield of dimethyl ether (unit=mol/g catalyst·hour) were calculated according to the methods disclosed in Preparation Example 1. Further, a yield of methanol (unit=mol/g catalyst·hour) and a yield of methyl (unit=mol/g catalyst·hour) were calculated by following equations:

Yield of methanol=$W_{MEOH}/W_{cat}$ wherein $W_{MEOH}$ denotes a yield of methanol per hour, and $W_{cat}$ denotes a weight of the catalyst.

Yield of methyl=$2 \times Y_{DME} + Y_{MEOH}$ wherein $Y_{DME}$ denotes a yield of dimethyl ether, and $Y_{MEOH}$ denotes a yield of methanol.

The experimental data showed that, when the medium oil of Example 3 was used to produce a mixture of dimethyl ether and methanol, very little lowering of the yield with time was observed, and the medium oil of Example 3 can bring an excellent result in the production of a mixture of dimethyl ether and methanol.

INDUSTRIAL APPLICABILITY

According to the medium oil of the present invention, a production efficiency of an oxygen-containing organic compound such as dimethyl ether can be enhanced, and can be maintained at a high level for a long term. This property is very advantageous in a production of an oxygen-containing organic compound such as dimethyl ether, which requires a high production efficiency.

As above, the present invention is explained with reference to particular embodiments, but modifications and improvements obvious to those skilled in the art are included in the scope of the present invention.

The invention claimed is:

1. A process of producing dimethyl ether, comprising a step of passing a mixture containing carbon monoxide and hydrogen through a catalyst slurry containing a mixture of
   (1) a medium oil selected from the group consisting of
      (a) a medium oil wherein a main component is a polybutene, and the number of paraffinic carbon atoms contained in the medium oil is 70% or more with respect to a total number of carbon atoms contained in the medium oil, and
      (b) a medium oil wherein a main component is a mixture of hydrocarbons of the formula (1):

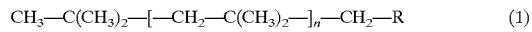

wherein R is —$CH(CH_3)_2$ or —$C(CH_3)=CH_2$, and n is 1 to 10, and the number of paraffinic carbon atoms contained in the medium oil is 70% or more with respect to a total number of carbon atoms contained in the medium oil,
   (2) a catalyst for synthesizing methanol, and
   (3) a catalyst for dehydrating methanol and a catalyst for shifting, or a catalyst for dehydrating methanol and shifting.

2. A process of producing a mixture of dimethyl ether and methanol, comprising a step of passing a mixture containing carbon monoxide and hydrogen through a catalyst slurry containing a mixture of
   (1) a medium oil selected from the group consisting of
      (a) a medium oil wherein a main component is a polybutene, and the number of paraffinic carbon atoms contained in the medium oil is 70% or more with respect to a total number of carbon atoms contained in the medium oil, and
      (b) a medium oil wherein a main component is a mixture of hydrocarbons of the formula (1):

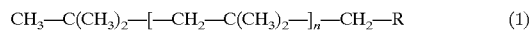

wherein R is —$CH(CH_3)_2$ or —$C(CH_3)=CH_2$, and n is 1 to 10, and the number of paraffinic carbon atoms contained in the medium oil is 70% or more with respect to a total number of carbon atoms contained in the medium oil,
   (2) a catalyst for synthesizing methanol, and
   (3) a catalyst for dehydrating methanol and a catalyst for shifting, or a catalyst for dehydrating methanol and shifting.

3. A slurry-bed reaction process comprising the step of performing a reaction in a catalyst slurry composed of a mixture of a solid catalyst and a medium oil selected from the group consisting of
   (a) a medium oil wherein a main component is a polybutene, and the number of paraffinic carbon atoms contained in the medium oil is 70% or more with respect to a total number of carbon atoms contained in the medium oil, and
   (b) a medium oil wherein a main component is a mixture of hydrocarbons of the formula (1):

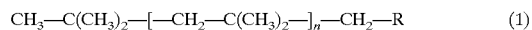

wherein R is —$CH(CH_3)_2$ or —$C(CH_3)=CH_2$, and n is 1 to 10, and the number of paraffinic carbon atoms contained in the medium oil is 70% or more with respect to a total number of carbon atoms contained in the medium oil.

* * * * *

Disclaimer 7,015,255—Keiji Tomura, Tokyo (JP); Takashi Ogawa, Tokyo (JP); Masami Ono, Tokyo (JP); Keiichi Okuyama, Tokyo (JP); Seiji Aoki, Tokyo (JP); Tsutomu Shikada, Tokyo (JP); Masatsugu Mizuguch, Tokyo (JP); and Yotaro Ohno, Tokyo (JP). MEDIUM OIL FOR SLURRY-BED REACTION PROCESS AND PROCESS OF PRODUCING DIMETHYL ETHER, Patent dated Mar. 21, 2006. Disclaimer filed December 15, 2009, by the owner JFE Holdings, Inc.

Hereby enter this disclaimer to the entire term of said patent.

*(Official Gazette, March 2, 2010)*

Disclaimer 7,015,255—Keiji Tomura; Takashi Ogawa; Masami Ono; Keiichi Okuyama; Seiji Aoki; Tsutomu Shikada; Masatsugu Mizuguchi; Yotaro Ohno, all of Japan. MEDIUM OIL FOR SLURRY-BED REACTION PROCESS AND PROCESS OF PRODUCING DIMETHYL ETHER. Patent dated Mar. 21, 2006. Disclaimer filed Feb. 4, 2002, by the assignee, JFE Holdings, Inc.

The term of this patent subsequent to the term of patent number 7,015,255 has been disclaimed.

*(Official Gazette, March 16, 2010)*